US008101268B2

(12) United States Patent
Miles et al.

(10) Patent No.: US 8,101,268 B2
(45) Date of Patent: *Jan. 24, 2012

(54) BONE SUBSTITUTE MATERIAL

(75) Inventors: Anthony William Miles, Bath (GB);
Irene Gladys Turner, Wiltshire (GB);
Jonathan Paul Gittings, Caerphilly (GB)

(73) Assignee: University of Bath, Bath (GB)

( * ) Notice: Subject to any disclaimer, the term of this patent is extended or adjusted under 35 U.S.C. 154(b) by 1022 days.

This patent is subject to a terminal disclaimer.

(21) Appl. No.: 10/568,201

(22) PCT Filed: Aug. 12, 2004

(86) PCT No.: PCT/GB2004/003475
§ 371 (c)(1),
(2), (4) Date: Sep. 20, 2006

(87) PCT Pub. No.: WO2005/016192
PCT Pub. Date: Feb. 24, 2005

(65) Prior Publication Data
US 2007/0106393 A1   May 10, 2007

(30) Foreign Application Priority Data
Aug. 12, 2003 (GB) .................................. 0318901.6

(51) Int. Cl.
*B32B 3/26* (2006.01)
*C04B 33/28* (2006.01)
*C04B 33/32* (2006.01)
*A61F 2/02* (2006.01)

(52) U.S. Cl. ............... 428/312.2; 428/315.5; 428/315.7; 623/23.56; 264/604; 264/628

(58) Field of Classification Search ............... 428/315.5, 428/315.7, 312.2; 623/23.5, 23.56; 264/628, 264/604
See application file for complete search history.

(56) References Cited

U.S. PATENT DOCUMENTS
4,192,021 A    3/1980   Deibig et al.
(Continued)

FOREIGN PATENT DOCUMENTS
CN      1068807      2/1993
(Continued)

OTHER PUBLICATIONS

Milosevski M. et al "Preparation and properties of dense and porous calcium phosphate" Ceramics International, Elsevier Applied Science Publ, Barking, Essex, GB vol. 25, No. 8, Dec. 1999 pp. 693-696.

(Continued)

*Primary Examiner* — Hai Vo
(74) *Attorney, Agent, or Firm* — Jackson Walker L.L.P.; Amy Ulfers Dunstan; Christopher J. Rourk

(57) ABSTRACT

A method of fabricating a bone substitute material comprises the steps of providing a foam material (3) having an open cell structure, distorting the shape of the foam material (3) and holding the material in a distorted shape, coating the walls of the cells of the foam material with a ceramic slip (5), removing the foam material, and sintering the ceramic slip to form a bone substitute material that is approximately a positive image of the distorted foam material (3). In another method, a granular bone material is formed from a multiplicity of pieces of foam that are not distorted.

22 Claims, 2 Drawing Sheets

U.S. PATENT DOCUMENTS

Figure 3A:
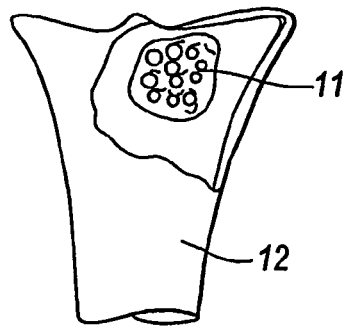

| | | | |
|---|---|---|---|
| 4,371,484 | A | 2/1983 | Inukai et al. |
| 4,600,546 | A | 7/1986 | Grundei |
| 4,810,685 | A * | 3/1989 | Twigg et al. ............ 502/60 |
| 5,769,897 | A | 6/1998 | Harle |
| 6,083,264 | A | 7/2000 | Wood et al. |
| 6,136,029 | A | 10/2000 | Johnson et al. |
| 6,302,913 | B1 | 10/2001 | Ripamonti et al. |
| 6,316,091 | B1 | 11/2001 | Richart et al. |
| 6,340,648 | B1 * | 1/2002 | Imura et al. ............ 501/80 |
| 2002/0022885 | A1 * | 2/2002 | Ochi ............ 623/16.11 |
| 2002/0165616 | A1 * | 11/2002 | Heide et al. ............ 623/23.56 |
| 2003/0138473 | A1 | 7/2003 | Koblish et al. |
| 2005/0049715 | A1 * | 3/2005 | Ito et al. ............ 623/23.5 |
| 2005/0158535 | A1 * | 7/2005 | Zhang et al. ............ 428/304.4 |
| 2006/0265081 | A1 | 11/2006 | Turner et al. |

FOREIGN PATENT DOCUMENTS

| | | | |
|---|---|---|---|
| EP | 254557 A2 * | 1/1988 | |
| EP | 1 329 229 A1 | 1/2003 | |
| JP | 64003047 | 1/1989 | |
| JP | 4193742 | 7/1992 | |
| JP | 4327525 | 11/1992 | |
| JP | 5327525 | 11/1992 | |
| WO | WO 9816267 | 4/1998 | |
| WO | WO 00/20353 | 4/2000 | |
| WO | WO 00/30998 | 6/2000 | |
| WO | WO 01/94274 A1 | 12/2001 | |
| WO | WO 02/11781 A1 | 2/2002 | |
| WO | WO 03/026714 A1 | 4/2003 | |
| WO | WO 2004065329 A1 | 8/2004 | |

OTHER PUBLICATIONS

Tancred, D.C. et al "A synthetic bone implant macroscopically identical to cancellous bone" Biomaterials, Elsevier Science Publishers BV, Barking, GB vol. 19, No. 24, Dec. 1998 pp. 2303-2311.

Fabbri, M. et al "Hydroxyapatite-based porous aggregates: physicochemical nature, structure, texture and architecture" CNR, research Institute for Ceramics Technology, Faenza, Italy, Biomaterials, vol. 16, No. 3, p. 225-228.

United States Patent and Trademark Office, Office Action, U.S. Appl. No. 10/543,247, Dec. 1, 2010.

United States Patent and Trademark Office, Office Action, U.S. Appl. No. 10/543,247, Mar. 16, 2010.

United States Patent and Trademark Office, Response to Restriction Requirement, U.S. Appl. No. 10/543,247, Dec. 1, 2010.

European Patent Office, International Search Report, PCT/GB2004/000253, Jul. 2, 2004.

European Patent Office, International Preliminary Report on Patentability, PCT/GB2004/000253, Jul. 29, 2005.

European Patent Office, Written Opinion of the International Searching Authority, PCT/GB2004/000253, Jul. 2, 2004.

* cited by examiner

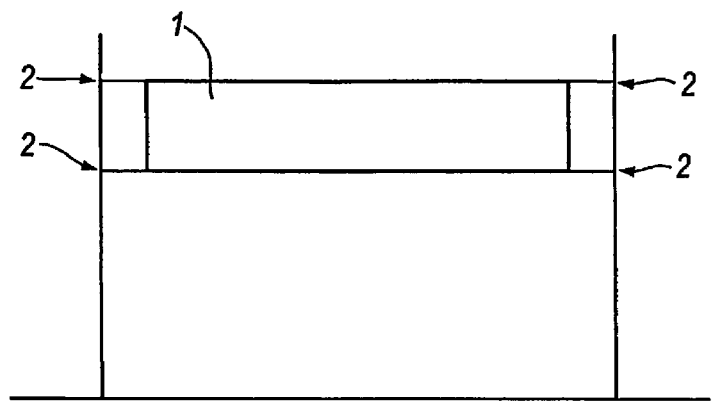
*Fig.1*
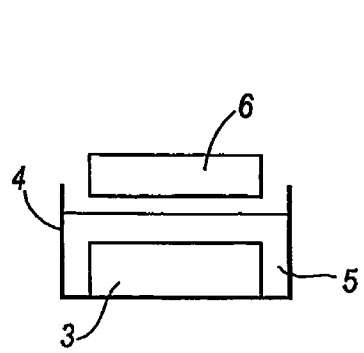 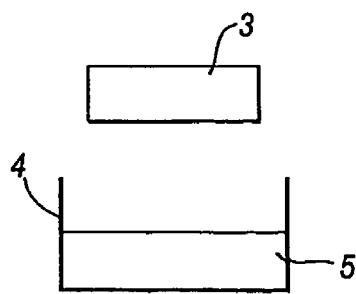 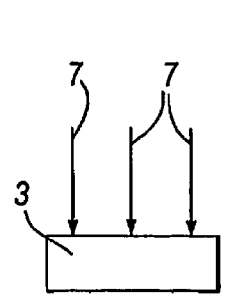
*Fig.2A*  *Fig.2B*  *Fig.2C*

BONE SUBSTITUTE MATERIAL

This invention relates to a method of fabricating a bone substitute material, to a bone substitute material that can be produced by such a method and to a method of forming a bone graft.

Various methods of fabricating bone substitute materials are known. The present invention provides novel methods of fabrication and novel materials that may advantageously be employed as bone substitute materials and have favourable physical properties. The invention also provides improvements to methods of forming bone grafts.

According to a first aspect of the invention there is provided a method of fabricating a bone substitute material, the method comprising the steps of:

providing a foam material having an open cell structure, distorting the shape of the foam material and holding the material in a distorted shape, coating the walls of the cells of the foam material with a ceramic slip, removing the foam material, and sintering the ceramic slip to form a bone substitute material that is approximately a positive image of the distorted foam material.

We have found that by adopting the method defined above it is possible to obtain an orientated bone substitute material with different strength characteristics in different directions. Natural bones also have orientated internal porous structures and the invention enables such natural structures to be reproduced more closely.

Reference is made herein to the bone substitute material being "approximately" a positive image of the foam material because it will not usually be an exact image. For example, usually the walls of the cells in the foam material will be solid whereas the walls of the cells of the bone substitute material will be hollow as a result of the removal of the foam material. On the other hand because the walls of the cells of the foam material are merely coated and are not filled, the bone substitute material is relatively close to being a positive image of the foam material and certainly is not a negative image.

The step of distorting the shape of the foam material preferably comprises stretching the foam material, preferably in one direction only. Such distortion provides a material with different strength characteristics in one direction than in the other two orthogonal directions and in that respect reproduces the structure of various natural bone materials. Conveniently, the foam material may be held in a stretched condition by clamps engaging opposite edge portions of the foam material. The clamps may be held apart at a selected distance, for example by a jig. The foam material may then be heated to deform the material and then cooled to retain the deformation permanently.

The degree of distortion of the foam can be chosen according to the degree of orientation required in the bone material. Typically the foam material is distorted by more than 20% in one direction. In an example of the invention described below the foam material is stretched by 30% in one direction.

The foam material may be removed by any suitable process. It is preferred, however, that the step of removing the foam material comprises heating the material. The foam material may be a polymeric foam material, for example a polyurethane foam material, and may be removed by combustion.

When the foam material is removed by heating, the method preferably comprises a first heating step in which the foam material is removed and a second, subsequent, heating step in which the ceramic slip is heated to a higher temperature and is sintered. Although the two heating steps may be merged into a single step, it is preferred that the first heating step is a gentle step allowing the foam material to be removed gradually. Preferably the temperature to which the filled foam material is heated does not exceed 800° C. Also, the temperature of the filled foam material is preferably increased slowly, preferably at a rate of less than 200° C./hr and more preferably less than 100° C./hr. For example, the filled foam material may be raised to a temperature of 600° C. at a rate of 30 to 60° C./hr in the first heating step; the material may then be maintained at a temperature of 600° C. for 1 hour.

The heating step for sintering, which is the second heating step in the case where there are first and second heating steps, preferably involves heating the material to over 1,000° C. Preferably the material is maintained at a temperature of over 1000° C. for more than 1 hour. In the example of the invention described below, the second heating step comprises raising the temperature from 600° C. to 1280° C. at a rate of 120° C./hr and then maintaining the material at 1280° C. for 4 hours. Subsequently the material is cooled to room temperature at the rate of 200° C./hr.

The step of coating the walls of the cells of the foam material with a ceramic slip may include the steps of immersing the foam material in the ceramic slip and draining some of the ceramic slip from the foam material. In order to obtain a thicker coating the immersing and draining steps may be repeated. The steps may be repeated six or more times but we have found that repeating the immersing and draining steps once produces good results.

Air may be directed, preferably at high velocity, onto the coated foam material, preferably onto all sides of the material, to inhibit the formation of closed cells.

In order to promote even coating of the cells throughout the volume of the foam material, the foam material may be mechanically compressed and then allowed to expand while it is immersed in the ceramic slip. That compression is of course a separate distortion of the foam material from the one that causes the product of the method to be orientated and is merely a temporary distortion to facilitate coating.

The sintered bone substitute material may be composed of any suitable ceramic material. Hydroxyapatite (HA, chemical formula $Ca_{10}(PO_4)_6(OH)_2$, Ca/P=1.67) is one of the preferred materials, together with tricalcium phosphate (TCP, Ca/P=1.50). In the example of the invention described below the sintered product is a mixture of HA and TCP.

The method preferably results in a bone substitute material having a macroporosity in the range of 40 to 70%. Macropores are hereby defined as pores having an equivalent diameter greater than 10 μm and therefore a material with a macroporosity of 40% has 40% of the space it occupies consisting of pores each of which have an equivalent diameter greater than 10 μm.

Preferably the material has many relatively large pores. Thus it is preferred that more than half of the macroporosity of the material is provided by pores having an equivalent diameter greater than 150 μm and preferably in the range of 150 to 450 μm.

For certain applications it is desirable to have a granular material. The method may therefore further comprise the step of breaking up the sintered bone substitute material into a plurality of separate pieces.

According to the first aspect of the invention there is further provided a bone substitute material comprising a porous sintered ceramic having approximately the form of a positive image of an open celled foam material, the walls defining the cells within the material being hollow, wherein the cellular structure is orientated such that the cells generally have a length in one direction greater than a length in a perpendicular direction.

The cells may be of generally elongate form having a length in one direction greater than their lengths in the two other perpendicular directions. Preferably, the cells have a length in one direction more than 20% greater than their lengths in the two other perpendicular directions.

The material preferably has a macroporosity in the range of 40% to 70%. More than half of the macroporosity of the material is preferably provided by pores having an equivalent diameter in the range of 150 to 450 μm. In an example of the invention almost 80% of the macroporosity of the material is provided by such pores.

Preferably the material has a breaking stress of more than 1 MPa, and preferably more than 2 MPa. Where reference is made to such a breaking stress, it should be understood that this is the breaking stress as measured by a three point bending test. Also, it is the minimum breaking stress of the material: it will be understood that in the case of an orientated material, the breaking stress will usually depend upon the direction of testing. In such a case, the breaking stress is to be regarded as the stress required to break the material when applied in a direction in which the material is strongest.

A balance has to be struck between macroporosity and breaking stress. As the macroporosity is increased so the breaking stress will reduce.

According to a second aspect of the invention, there is provided a method of fabricating a granular bone substitute material, the method comprising the steps of:

providing a multiplicity of pieces of foam material having an open cell structure, each occupying a space of less than 1000 mm$^3$, coating the walls of the cells of the pieces of foam material with a ceramic slip, removing the foam material, and sintering the ceramic slip to form a granular bone substitute material in which the granules are approximately positive images of the pieces of foam material.

By taking the surprising step of using a multiplicity of pieces of foam material, rather than using a single larger piece of material, and then breaking up the sintered product into a multiplicity of pieces, we have found that it is possible to produce a granular product in which each of the granules can be of a controlled size and shape.

The pieces of foam material are preferably relatively small and may have a maximum dimension of less than 12 mm. The pieces of foam material may easily be formed from a larger piece of material, for example by cutting up the foam material. The pieces may be cut up into irregular or regular shapes, for example of approximately cuboidal shape. The pieces of foam material may be approximately cubes. In that case the cubes preferably have sides of length less than 8 mm. It is possible to provide pieces of foam material of varying sizes, resulting in a granular material in which the granules vary in size. Alternatively the pieces of foam material may be all of substantially the same size. Similarly, the pieces of foam may be all of substantially the same shape or of different shapes. A variety of sizes of granule promotes close packing but it may also be desirable to supply the granules in a series of ranges of size with relatively little size variation within each range. A purchaser can then select whatever mixture of sizes is appropriate for a particular application.

If desired, the granular sintered material may be treated to reduce the size and/or alter the shape of the granules. For example, the material may be subjected to a milling step, which may comprise ball milling. Such milling may, for example, be carried out in order to round the edges and corners of the granules.

The foam material may be removed by any suitable process. It is preferred, however, that the step of removing the foam material comprises heating the material. The foam material may be a polymeric foam material, for example a polyurethane foam material, and may be removed by combustion.

When the foam material is removed by heating, the method preferably comprises a first heating step in which the foam material is removed and a second, subsequent, heating step in which the ceramic slip is heated to a higher temperature and is sintered. Although the two heating steps may be merged into a single step, it is preferred that the first heating step is a gentle step allowing the foam material to be removed gradually. Preferably the temperature to which the filled foam material is heated does not exceed 800° C. Also, the temperature of the filled foam material is preferably increased slowly, preferably at a rate of less than 200° C./hr and more preferably less than 100° C./hr. For example, the filled foam material may be raised to a temperature of 600° C. at a rate of 30 to 60° C./hr in the first heating step; the material may then be maintained at a temperature of 600° C. for 1 hour.

The heating step for sintering, which is the second heating step in the case where there are first and second heating steps, preferably involves heating the material to over 1000° C. Preferably the material is maintained at a temperature of over 1000° C. for more than 1 hour. In the example of the invention described below, the second heating step comprises raising the temperature from 600° C. to 1280° C. at a rate of 120° C./hr and then maintaining the material at 1280° C. for 4 hours. Subsequently the material is cooled to room temperature at the rate of 200° C./hr.

The step of coating the walls of the cells of the pieces of foam material with a ceramic slip may include the steps of immersing the pieces of foam material in the ceramic slip and draining some of the ceramic slip from the pieces of foam material. In order to obtain a thicker coating the immersing and draining steps may be repeated. The steps may be repeated six or more times but we have found that repeating the immersing and draining steps once produces good results.

The step of draining some of the ceramic slip from the pieces of foam material may comprise the step of supporting the pieces of foam material on a perforated support surface. For example, the pieces of foam material may be placed in a sieve and may be shaken.

In order to promote even coating of the cells throughout the volume of the pieces of foam material, the pieces may be mechanically compressed and then allowed to expand while they are immersed in the ceramic slip.

The sintered bone substitute material may be composed of any suitable ceramic material.

Hydroxyapatite (HA, chemical formula $Ca_{10}(PO_4)_6(OH)_2$, Ca/P=1.67) is one of the preferred materials, together with tricalcium phosphate (TCP, Ca/P=1.50). In the example of the invention described below the sintered product is a mixture of HA and TCP.

Air may be directed, preferably at high velocity, onto the coated foam material, preferably onto all sides of the material, to inhibit the formation of closed cells.

The method preferably results in a granular bone substitute material having a macroporosity in the range of 40 to 70%.

Preferably the material has many relatively large pores. Thus it is preferred that more than half of the macroporosity of the material is provided by pores having an equivalent diameter greater than 150 μm and preferably in the range of 150 to 450 μm.

According to the second aspect of the invention there is also provided a granular bone substitute material comprising a multiplicity of granules of a porous sintered ceramic, each granule having approximately the form of a positive image of an open celled foam material, the walls defining the cells within the granules being hollow and the granule occupying a space of less than 1000 mm$^3$.

The granular bone substitute material may have a compressive modulus at a load of 500 N of more than 40 MPa and/or it may have a compressive modulus at a load of 1000 N of more than 60 MPa. The compressive modulus is measured by a standard die plunger test.

As mentioned above, materials of the first and second aspects of the invention may possess an especially good combination of macroporosity and breaking stress. Indeed, a third aspect of the invention is characterized by such properties. Thus, according to a third aspect of the invention, there is provided a bone substitute material of a porous sintered ceramic having approximately the form of a positive image of an open celled foam material, the material having a macroporosity in the range of 40 to 70% and a breaking stress of more than 1 MPa.

According to a fourth aspect of the invention, there is provided a method of forming a bone graft comprising the steps of implanting a bone substitute material that is approximately in the form of a positive image of an open celled foam material into or onto a bone.

The bone substitute material may be a granular material and may be of the kind defined above. The material may be implanted into a bone and substantially entirely enclosed therein, but it may also be implanted into a recess on the surface of a bone.

Alternatively the bone substitute material may be in a single piece and may be of the kind defined above. In one example, the material is in the form of a cylindrical block, which may be of circular cross-section. Such a block may be implanted into a spine of a person or animal. The material may be in the form of a preshaped block and may be implanted into a correspondingly shaped space in or on the surface of a bone, for example in the case of a condylar defect. The implant may contribute to the structural strength of the bone, and may even provide most of the structural strength in a region of the bone. The implant may provide a scaffold into which or onto which bone can grow. In some applications it may be desirable to place the material in a cage or other structure which is then implanted.

Whilst various features have been described with reference to particular aspects of the invention, it should be understood that such features may where appropriate be applied to other aspects of the invention. For example the bone material according to the second aspect of the invention may be in the form of a cylindrical block which may be of circular cross-section. Also a feature described with reference to a method of fabricating a material may also where appropriate be applied to the material and vice versa.

By way of example certain embodiments of the invention will now be described with reference to the accompanying drawings, in which:

FIG. 1 is a schematic drawing of a device for use in a first part of a method of fabricating a bone substitute material, FIGS. 2A to 2C are schematic drawings illustrating subsequent parts of a method of fabricating a bone substitute material, and FIGS. 3A to 3F are schematic drawings illustrating certain applications of materials embodying the invention.

Exemplary methods of fabricating a bone substitute material are described below and employ two starting materials: firstly, an organic foam material having an open cell structure with each cell connecting to each neighbouring cell; secondly, a ceramic slip.

A first exemplary method is carried out using the device shown schematically in FIG. 1. A rectangular sheet 1 of open cell foam material (for example, measuring 240 mm×80 mm×25 mm) is held by G-clamps 2 which grip opposite ends of the material and are held apart from one another at such a spacing that the sheet of material is lengthened to a total length of about 30% more than its natural length. While the block 1 is held in position it is placed in an air flowing oven for a period of time and then removed and placed in an air flow chamber (with the air at room temperature) for a further period of time. In a particular example the air in the oven is at 150° C. and the block is placed in each location for 15 minutes. The effect of the treatment is to introduce a permanent deformation in the foam material. The pores in the material, which were originally of mainly spherical shape, become of ellipsoidal shape.

The stretched foam material is cut into pieces measuring in a particular example 40 mm×25 mm×10 mm and placed overnight in distilled water and then allowed to dry ready for slip impregnation. Referring now to FIG. 2A, a piece of foam material 3 is inserted into the female part 4 of a mechanical plunging machine which contains ceramic slip 5. The male part 6 of the plunger is then lowered and pushes air and slip out of the material. On retraction of the plunger 6 the foam material 3, which is fully immersed in the slip 5, has the slip drawn into it coating the walls of the cells of the foam material. Those walls may be viewed as struts within the material. The process of lowering and then retracting the plunger is repeated once.

The foam material 3 is then held above the female part 4 as illustrated in FIG. 2B and slip is allowed to seep out of the foam leaving the cells mainly full of air but with the cell walls coated by the slip. The foam material is placed on tissue paper to remove any excess moisture.

The coated foam material 3 is then sprayed on all sides with high velocity compressed air as illustrated by arrows 7 in FIG. 2C to reduce the likelihood of closed cells forming, to promote even coating of the cell walls and to dry the ceramic slip. To complete this stage of the process, the material is placed in an airflow oven at 120° C. for six hours in order to ensure it is moisture free.

The coated foam material is then slowly heated from room temperature to cause the organic foam to decompose slowly and completely by combustion, the products of the decomposition being allowed to escape. The heating is then increased substantially to sinter the ceramic slip and form the bone substitute material. In examples, the temperature was increased at the rate of 30 to 60° C. per hour from room temperature, until a temperature of 600° C. was reached. The oven was then held at a temperature of 600° C. for 1 hour to complete a first stage of heating. During this slow and relatively gentle heating all of the polyurethane foam decomposed, and the green porous material was left. The temperature of the oven was then further increased for a second stage of heating at the rate of 120° C. per hour until it reached 1280° C. The temperature was maintained at 1280° C. for 4 hours and then cooled to room temperature at the rate of 200° C. per hour. At the end of the second stage of heating the sintered material had been formed.

The bone substitute material produced after sintering has a good combination of strength and porosity. Furthermore the stretching of the foam material results in an orientated material with a selected degree of elongation of the pores in the foam material and in the sintered product. The macroporosity of the product was measured using image analysis combined with the Optimas 6.1 imaging software and showed the following results in one particular example:

| Pore range (μm) | Total % of porosity |
|---|---|
| 10-15 | 12.5 |
| 150-450 | 79.3 |
| 450+ | 8.2 |

The exemplary method described above was modified to produce a granular material. The step of stretching the foam material was omitted and the foam material was cut up into cubes the sides of which had lengths in the range of 2 to 4 mm. The cubes were coated in substantially the same manner as described above and then shaken gently in a sieve to drain ceramic slip from them. They were then dried and heated in the same manner as described above. After sintering the granules were placed in a polyethylene container together with zirconia milling media and ball milled for 6 hours. The milling rounded off the edges of the granules.

The procedures described above were carried out with foams of different pore sizes including 20, 30 and 45 ppi (pores per inch).

The macroporosity of the granules produced in this way was similar to that indicated above. The compressive modulus of the granules was tested using a standard die plunger test. The material was compacted into a die, loaded up to 500 N, then relaxed, taken up to 1000 N and then relaxed. The results with a foam material of 30 ppi were a modulus of 49.6 MPa when loaded up to 500 N and a modulus of 66.5 MPa when loaded up to 1000 N.

Figure 3B:
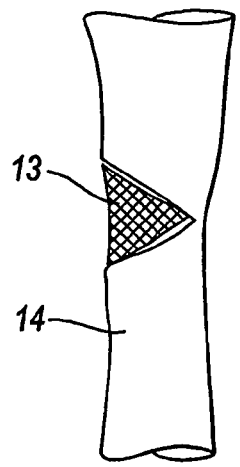
Figure 3C:
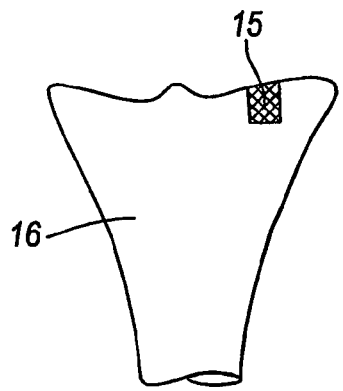
Figure 3D:
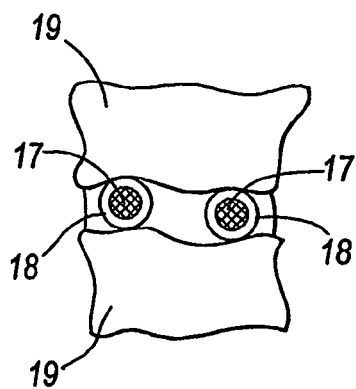
Figure 3E:
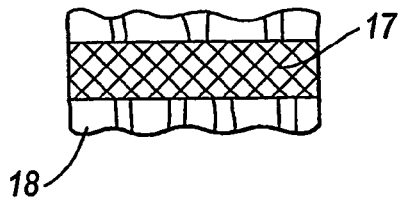
Figure 3F:
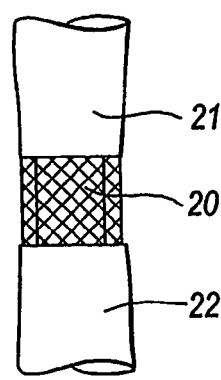

The bone substitute materials described above may be used in many different ways. FIGS. 3A to 3F provide some examples of applications of the materials. In FIG. 3A granular bone substitute material 11 is shown grafted in a bone 12 and enclosed within the bone. In FIG. 3B a single piece of bone substitute material 13 which has been formed into a desired shape by machining of the sintered product, is shown implanted in a bone 14 to deal with an uncontained defect in the bone. Similarly in FIG. 3C, a preformed plug 15 of bone substitute material is shown grafted into a bone 16 to deal with a condylar defect. FIGS. 3D and 3E show the use of cylindrical pieces of sintered bone substitute material in a spinal application. FIG. 3D shows the general arrangement with two cylindrical pieces 17 of bone substitute material housed in cylindrical cages 18 which are located between vertebral bodies 19. FIG. 3E is a sectional view through one of the cages 18 that is housing a piece 17 of substitute material. The cage is of a kind known per se and has circumferential grooves. Finally, in FIG. 3F a preformed piece 20 of sintered bone substitute material is shown acting as a structural graft between two pieces of bone 21, 22.

The invention claimed is:

1. A method of fabricating a bone substitute material, the method comprising the steps of:
   providing a foam material having an open cell structure,
   distorting the shape of the foam material and holding the material in a distorted shape,
   coating the walls of the cells of the foam material with a ceramic slip,
   removing the foam material, and
   sintering the ceramic slip to form a bone substitute material, wherein the bone substitute material comprises a porous sintered ceramic, the porous sintered ceramic being composed from hydroxyapatite or tricalcium phosphate, and the porous sintered ceramic having approximately the form of a positive image of an open celled foam material, the walls defining the cells within the material being hollow such that each wall defining cells has two wall ceramic material layers and a hollow cavity extending between the two wall ceramic material layers, wherein the cellular structure is orientated such that the cells are elongated, having a length in one direction greater than their lengths in the two other perpendicular directions and wherein the bone substitute material has a breaking stress of more than 1 MPa.

2. A method according to claim 1, in which the step of distorting the shape of the foam material comprises stretching the foam material.

3. A method according to claim 2, in which the foam material is stretched in one direction only.

4. A method according to claim 2, in which the foam material is permanently deformed.

5. A method according to claim 1, in which the step of removing the foam material comprises heating the material.

6. A method according to claim 5, in which the method comprises a first heating step in which the foam material is removed and a second, subsequent, heating step in which the ceramic slip is heated to a higher temperature and is sintered.

7. A method according to any preceding claim, in which the step of coating the walls of the cells of the foam material with a ceramic slip includes the steps of immersing the foam material in the ceramic slip and draining some of the ceramic slip from the foam material.

8. A method according to claim 7, in which the immersing and draining steps are repeated.

9. A method according to claim 7, in which the foam material is mechanically compressed and then allowed to expand while it is immersed in the ceramic slip.

10. A method according to claim 7, in which air is directed onto the coated foam material to inhibit the formation of closed cells.

11. A method according to claim 1, in which the foam material is a polymeric foam material.

12. A method according to claim 1, in which the ceramic base substitute material has a macroporosity in the range of 40 to 70%.

13. A method according to claim 1, in which more than half of the macroporosity of the material is provided by pores having an equivalent diameter in the range of 150 to 450 μm.

14. A bone substitute material comprising a porous sintered ceramic, the porous sintered ceramic being composed from hydroxyapatite or tricalcium phosphate, and the porous sintered ceramic having approximately the form of a positive image of an open celled foam material, the walls defining the cells within the material being hollow such that each wall defining cells has two wall ceramic material layers and a hollow cavity extending between the two wall ceramic material layers, wherein the cellular structure is orientated such that the cells are elongated, having a length in one direction greater than their lengths in the two other perpendicular directions and wherein the bone substitute material has a breaking stress of more than 1 MPa.

15. A bone substitute material according to claim 14, in which the cells have a length in one direction more than 20% greater than their length in the two other perpendicular directions.

16. A bone substitute material according to claim 14, in which the material has a macroporosity in the range of 40 to 70%.

17. A bone substitute material according to claim 14, in which more than half of the macroporosity of the material is provided by pores having an equivalent diameter in the range of 150 to 450 µm.

18. A method of forming a bone graft comprising the steps of implanting a bone substitute material into or onto a bone, wherein the bone substitute material comprises a porous sintered ceramic, the porous sintered ceramic being composed from hydroxyapatite or tricalcium phosphate, and the porous sintered ceramic having approximately the form of a positive image of an open celled foam material, the walls defining the cells within the material being hollow such that each wall defining cells has two wall ceramic material layers and a hollow cavity extending between the two wall ceramic material layers, wherein the cellular structure is orientated such that the cells are elongated, having a length in one direction greater than their lengths in the two other perpendicular directions and wherein the bone substitute material has a breaking stress of more than 1 MPa.

19. A method according to claim 18, in which the bone substitute material is in the form of a cylindrical block of circular cross-section.

20. A method according to claim 18, in which the material is in the form of a preshaped block and is implanted into a correspondingly shaped space in or on the surface of a bone.

21. A method according to claim 20, in which the implant contributes to the structural strength of the bone.

22. A method according to claim 18, in which the material is housed in a cage or other structure which is then implanted.

* * * * *